US009568381B2

(12) United States Patent
Daniecki et al.

(10) Patent No.: US 9,568,381 B2
(45) Date of Patent: Feb. 14, 2017

(54) LOWER LIMB FORCE SENSING SYSTEM (71) Applicants: Henry J. Daniecki, Cream Ridge, NJ (US); S. R. Rozbruch, Harrison, NY (US); David C. Goral, Bayville, NJ (US)

(72) Inventors: Henry J. Daniecki, Cream Ridge, NJ (US); S. R. Rozbruch, Harrison, NY (US); David C. Goral, Bayville, NJ (US)

(*) Notice: Subject to any disclaimer, the term of this patent is extended or adjusted under 35 U.S.C. 154(b) by 104 days.

(21) Appl. No.: 14/711,371

(22) Filed: May 13, 2015

(65) Prior Publication Data
US 2015/0330855 A1 Nov. 19, 2015

Related U.S. Application Data (60) Provisional application No. 61/993,548, filed on May 15, 2014, provisional application No. 62/051,588, filed on Sep. 17, 2014.

(51) Int. Cl.
G01L 9/06 (2006.01)
G01L 5/00 (2006.01)
G01L 9/00 (2006.01)
G01L 19/14 (2006.01)
A43D 1/00 (2006.01)
G01L 9/18 (2006.01)
A43B 3/00 (2006.01)
A43B 17/00 (2006.01)
A61B 5/00 (2006.01)
G01L 1/16 (2006.01)

(52) U.S. Cl.
CPC ........... G01L 5/0038 (2013.01); A43B 3/0005 (2013.01); A43B 17/00 (2013.01); A43D 1/00 (2013.01); A61B 5/6807 (2013.01); G01L 9/0052 (2013.01); G01L 9/18 (2013.01); G01L 19/147 (2013.01); G01L 1/16 (2013.01)

(58) Field of Classification Search
CPC ..................................................... G01L 5/0038
See application file for complete search history.

(56) References Cited

U.S. PATENT DOCUMENTS

| 5,033,291 A * | 7/1991 | Podoloff ................. G01L 1/205 73/172 |
| 5,107,854 A | 4/1992 | Knotts et al. |
| 5,253,654 A | 10/1993 | Thomas et al. |
| 5,269,081 A | 12/1993 | Gray |
| 5,323,650 A | 6/1994 | Fullen et al. |
| 5,619,186 A | 4/1997 | Schmidt et al. |

(Continued)

Primary Examiner — Ryan Walsh
(74) Attorney, Agent, or Firm — Fox Rothschild LLP; Robert J. Sacco; Carol E. Thorstadt-Forsyth (57) ABSTRACT Lower limb force sensing system includes a sensory insole formed of a plurality of thin film material layers arranged in a stack to form a plurality of sensor cells in a pattern that defines a sensor array. A plurality of perforations defined in the thin film material layers extend substantially around a perimeter of each sensor cell to substantially separate each sensor cell from a remainder of the thin film material layers and form a hinge member which extends from each sensor cell to an interstitial portion of the thin film layers extending between adjacent ones of the sensor cells. The hinge member defines an axis of rotation about which the sensor cell can pivot independently relative to adjacent interstitial portions of the thin film material layers.

21 Claims, 11 Drawing Sheets (56) References Cited

U.S. PATENT DOCUMENTS

| | | | | |
|---|---|---|---|---|
| 6,155,120 | A * | 12/2000 | Taylor | A61B 5/1036 |
| | | | | 73/862.046 |
| 6,174,294 | B1 | 1/2001 | Crabb et al. | |
| 6,195,921 | B1 * | 3/2001 | Truong | A43B 3/00 |
| | | | | 340/573.1 |
| 6,836,744 | B1 * | 12/2004 | Asphahani | A43D 1/02 |
| | | | | 377/24.2 |
| 7,355,519 | B2 | 4/2008 | Grold et al. | |
| 7,395,717 | B2 * | 7/2008 | DeAngelis | G01L 1/146 |
| | | | | 73/724 |
| 7,726,206 | B2 | 6/2010 | Terrafranca, Jr. et al. | |
| 7,771,371 | B2 | 8/2010 | Avni | |
| 8,460,218 | B2 | 6/2013 | Fenkell | |
| 8,479,585 | B2 * | 7/2013 | Shaw-Klein | H01L 41/081 |
| | | | | 73/777 |
| 8,639,455 | B2 | 1/2014 | Horst et al. | |
| 8,676,541 | B2 | 3/2014 | Schrock et al. | |
| 8,870,795 | B2 * | 10/2014 | Kim | A61B 5/1038 |
| | | | | 600/587 |
| 2007/0245504 | A1 * | 10/2007 | Spector | A43B 17/00 |
| | | | | 12/142 N |
| 2010/0168622 | A1 | 7/2010 | Dar et al. | |
| 2013/0165817 | A1 * | 6/2013 | Horst | A61F 5/0102 |
| | | | | 600/587 |
| 2013/0213147 | A1 | 8/2013 | Rice et al. | |
| 2013/0275057 | A1 * | 10/2013 | Perlin | G06F 3/0414 |
| | | | | 702/41 |
| 2014/0182170 | A1 * | 7/2014 | Wawrousek | A43B 7/14 |
| | | | | 36/103 |
| 2015/0296922 | A1 * | 10/2015 | Rushbrook | A43B 23/16 |
| | | | | 36/68 |
| 2015/0331524 | A1 * | 11/2015 | McMillen | G06F 3/0414 |
| | | | | 345/174 |
| 2015/0370398 | A1 * | 12/2015 | Perlin | G06F 3/0414 |
| | | | | 345/173 |
| 2016/0147353 | A1 * | 5/2016 | Filiz | G01L 1/18 |
| | | | | 345/174 |
| 2016/0252412 | A1 * | 9/2016 | McMillen | G01L 1/18 |
| 2016/0287937 | A1 * | 10/2016 | Fitzgerald | A63B 24/0062 |
| 2016/0299021 | A1 * | 10/2016 | Thillainadarajah | G01L 5/16 |

* cited by examiner

LOWER LIMB FORCE SENSING SYSTEM

CROSS REFERENCE TO RELATED APPLICATIONS

This application claims priority benefit of Provisional Patent Application No. 61/993,548 filed May 15, 2014, and Provisional Patent Application No. 62/051,588 filed Sep. 17, 2014, the entirety of which disclosures are incorporated herein by reference.

BACKGROUND OF THE INVENTION

Statement of the Technical Field

The inventive arrangements relate to force monitoring systems and more particularly to devices which are used to monitor forces applied through a lower limb of a person.

Description of the Related Art

Lower limb force measuring systems can measure a load or force which is applied to a lower limb through a foot. These systems are used in a wide variety of situations where a medical condition necessitates that a force or load applied to a lower body extremity (or prosthetic) is to be limited to some predetermined level. Such situations may arise, for example, during rehabilitation therapy after surgery or injury to the hips, knees, ankles or other portions of the lower body. Lower limb force measuring systems as described herein can also be used in other health and fitness monitoring situations involving walking, running, or jumping activities. In each of these scenarios, it may be necessary to carefully measure the force exerted upon a lower limb.

Lower limb force monitoring systems can include a sensor portion and a monitoring portion. The sensor portion usually comprises a force sensitive means that is positioned beneath the sole of the foot. The force sensitive means can be comprised of an insole for a shoe. Accordingly, an insole as described herein may have the shape of a conventional shoe insole. The actual force sensing is performed by one or more force sensors which are incorporated into the insole. The sensor portion of a force measuring system as described herein can be connected to an electronic control system. The control system receives electrical signals from the force sensitive means and can include a battery to power the system. The control system can also include an alarm circuit. The alarm circuit can include an audio transducer (e.g. a buzzer) that is triggered when the force level measured by the sensor exceeds a predetermined limit. In some such systems, the predetermined limit can be adjusted by a user to accommodate the needs of different individuals.

SUMMARY OF THE INVENTION

Embodiments of the invention concern a lower limb force sensing system. The system includes a sensory insole formed of a plurality of thin film material layers arranged in a stack. The stack is arranged to form a plurality of sensor cells in a pattern that defines a sensor array. Each of the sensor cells is comprised of a pressure sensitive pad disposed between opposing top and bottom electrically conductive layers. For example, a pressure sensitive pad as described herein can be comprised of a piezoresistive material. A plurality of perforations defined in the thin film material layers extend substantially around a perimeter of each sensor cell to substantially separate each sensor cell from a remainder of the thin film material layers forming the sensory insole. However, the plurality of perforations also define for each sensor cell at least one hinge member which extends from each sensor cell to an interstitial portion of the thin film layers extending between adjacent ones of the sensor cells. The hinge member comprises electrical connections respectively between portions of the top and bottom electrically conductive layers disposed in the interstitial portion of the thin film layers and the top and bottom electrically conductive layers disposed within the perimeter of each sensor cell. The hinge member also defines an axis of rotation about which the sensor cell can pivot independently relative to adjacent interstitial portions of the thin film material layers. The thin film material layers can further include top and bottom outermost layers formed of a low-coefficient of friction material. For example, at least one of the top and bottom outermost layers can be formed of ultra-high-molecular-weight polyethylene (UHMWPE).

According to one aspect, the top and bottom electrically conductive layers extend coextensive with the sensor array to provide continuity to the electrical connections of each of the sensor cells. The sensor cells are connected in parallel between the top and bottom electrically conductive layers. With the foregoing arrangement, the top and bottom electrically conductive layers maintain continuity with the electrical connections of all the sensor cells on a remaining portion of the sensory insole when unwanted portions of the material layers of the sensory insole have been cut away from the remaining portion.

The system also includes a control unit remote from the sensory insole. The control unit detects electrical changes occurring within the plurality of sensor cells responsive to changes in force applied to the sensory insole. In this regard, the control unit can be electrically connected to the sensory insole with only two electrical conductors. These can include a first electrical conductor connected to the top electrically conductive layer and a second electrical conductor connected to the bottom electrically conductive layer. According to one aspect, the remote control system can be removably electrically connected to the two conductors using a jack and plug arrangement.

In an exemplary arrangement described herein, the electrical characteristic which is varied responsive to changes in force is a resistance between the top and bottom electrically conductive layers. In this regard, the control unit can comprise a regulated voltage source which is connected to two electrical conductors and a processing device which determines a force exerted on the sensory insole responsive to variations in voltage drop occurring across the two electrical conductors.

The control unit can include a data storage device and at least one wireless transceiver for communicating pressure data stored in the data storage device by the processing device to a remote computing device. The control unit can also include at least one progression bar comprised of a plurality of illuminable elements which progressively illuminate in response to increases in force applied to the sensory insole. Further, the control unit can include an auditory device which is responsive to the processing device to produce an auditory signal when a predetermined force applied to the sensory insole has been met or exceeded.

According to another aspect, the invention concerns a method for improving measurement accuracy when using a sensory insole. The method involves providing a sensory insole formed of a plurality of thin film material layers arranged in a stack. The stack is arranged to form a plurality of sensor cells in a pattern to define a sensor array, where each of the sensor cells is comprised of a pressure sensitive pad disposed between opposing top and bottom electrically conductive layers. The process further involves forming a plurality of perforations in the thin film material layers which extend substantially around a perimeter of each sensor cell to substantially separate each sensor cell from a remainder of the thin film material layers forming the sensory insole. The perforations also define at least one hinge member for each sensory cell which extends from each sensor cell to an interstitial portion of the thin film layers extending between adjacent ones of the sensor cells. Thereafter, one or more of the plurality of sensor cells is pivoted independently relative to adjacent interstitial portions of the thin film material layers when the sensory insole is placed in footwear, the pivoting occurring about an axis of rotation defined by the at least one hinge member in response to flexing of the user's foot.

The method can also comprise reducing a pressure measurement error associated with the sensory insole by including in the plurality of thin film material layers top and bottom outermost layers formed of a low-coefficient of friction material. For example, the low-coefficient of friction material can be chosen to be an ultra-high-molecular-weight polyethylene (UHMWPE).

BRIEF DESCRIPTION OF THE DRAWINGS

Embodiments will be described with reference to the following drawing figures, in which like numerals represent like items throughout the figures, and in which.

DETAILED DESCRIPTION

The invention is described with reference to the attached figures. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operation are not shown in detail to avoid obscuring the invention. The invention is not limited by the illustrated ordering of acts or events, as some acts may occur in different orders and/or concurrently with other acts or events. Furthermore, not all illustrated acts or events are required to implement a methodology in accordance with the invention.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

Figure 1:
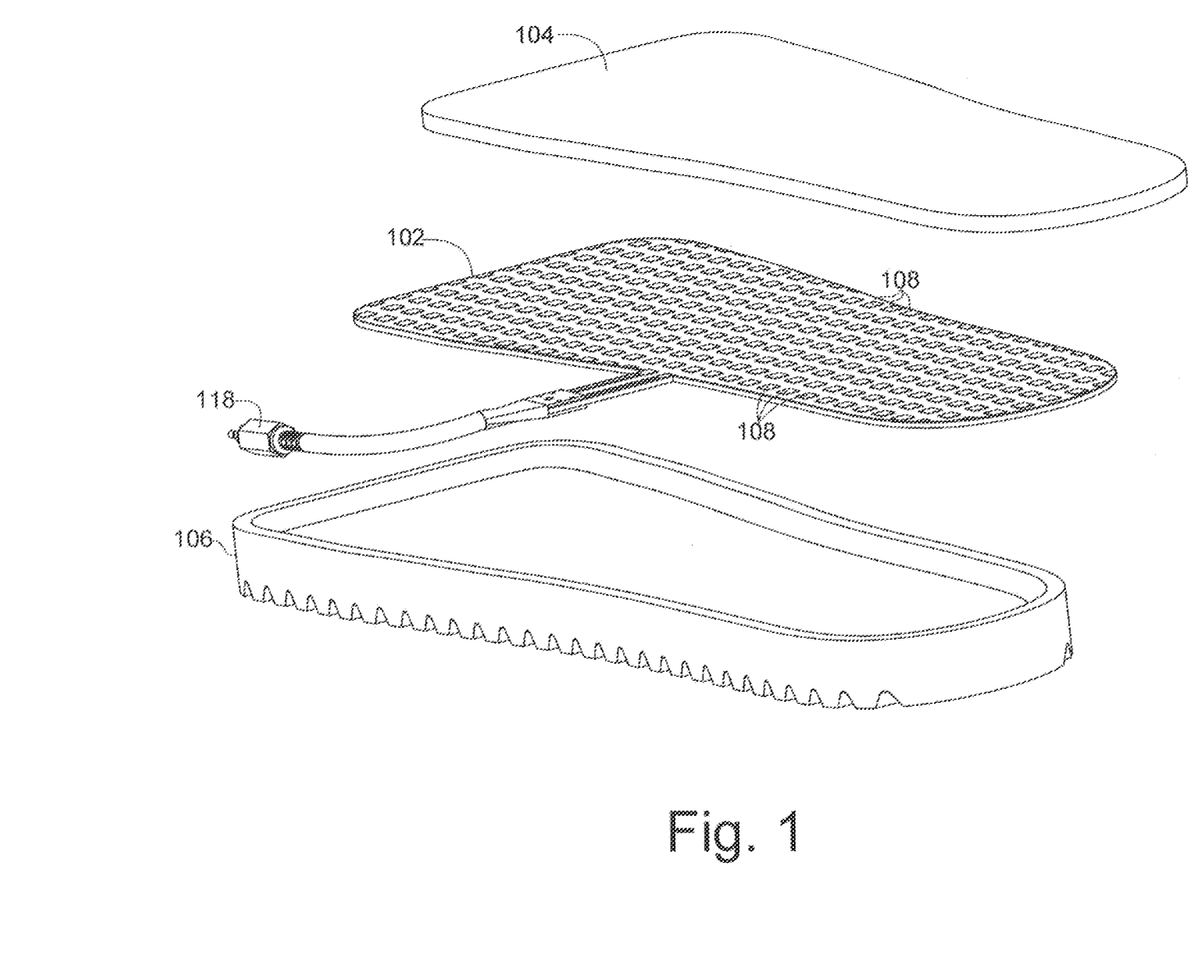
FIG. 1 shows an exemplary sensory insole according to the inventive arrangements.

Referring now to FIG. 1, a sensory insole 102 according to the inventive arrangements can be placed between a conventional footwear insole 104 and the sole 106 of the appropriate footwear. The sensory insole 102 is comprised of a periodic pattern of sensor cells 108 which are part of an integrated sensor array. The arrangement of the sensor cells 108, their periodic pattern, and a plurality of layers comprising the sensory insole provide numerous advantages as compared to conventional systems. Each of the foregoing aspects of the sensory insole 102 will now be described in further detail. Each of the sensor cells which are arranged in the periodic pattern comprising the sensor array have a common or shared design which can be more clearly understood with reference to FIG. 2.

Figure 2:
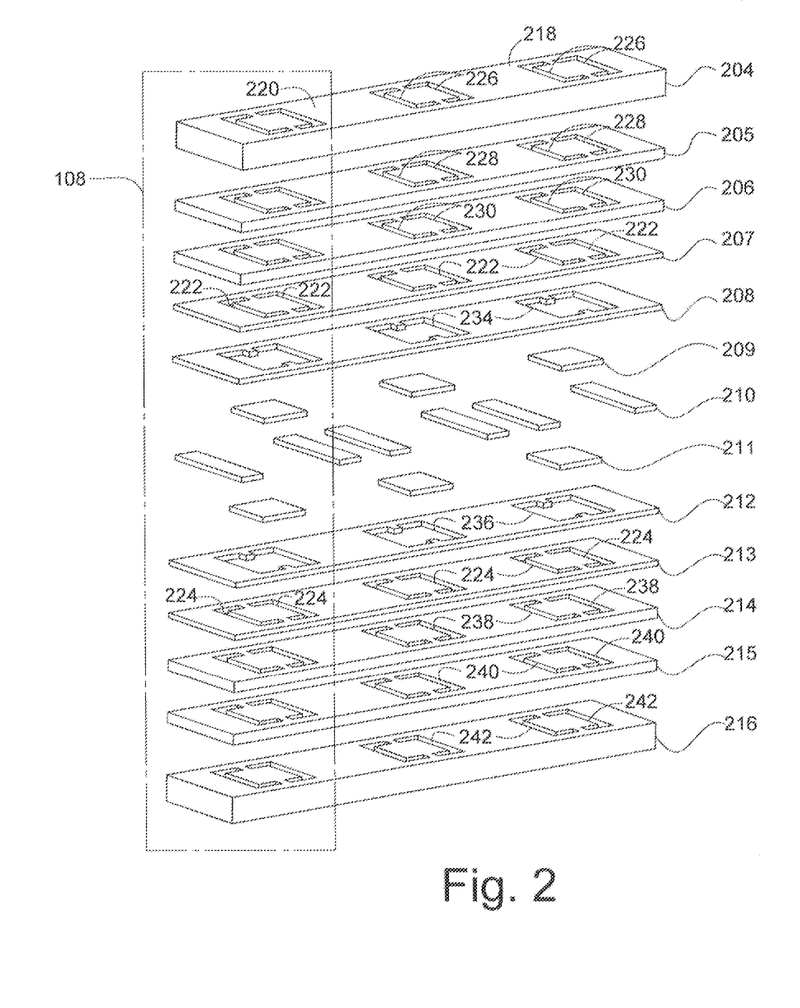
FIG. 2 is an exploded view of a portion of the sensory insole in FIG. 1 that is useful for understanding the invention.

The exemplary section of the sensor array shown in FIG. 2 includes three individual sensor cells 108 from the periodic array of sensor cells comprising the sensory insole. For clarity in disclosing the invention, the exemplary section is shown in FIG. 2 as separate from the remaining cells in the sensor array. But it should be understood that in actual practice, such exemplary section would be formed as an integral part of larger continuous sheet of sensor cells which comprise the sensory insole. According to one aspect of the invention, the continuous array of sensor cells described herein will advantageously extend across substantially the entire surface of the sensory insole.

As may be observed in FIG. 2, the sensory insole 102 is comprised of a plurality of thin film material layers. The outermost layers 204, 216 are comprised of a material specifically chosen for its low coefficient of friction, self-lubrication, strength and durability properties. According to one aspect, a low-coefficient of friction material suitable for this purpose can have a static coefficient of friction in the range of between about 0.1 and 0.20. For example, these outermost layers can advantageously be formed of a polyolefin material such as ultra-high-molecular-weight polyethylene (UHMWPE) or similar sheets. The outermost layers 204, 216 are respectively fastened to sensor substrate layers 206, 214 using adhesive layers 205, 215. Any suitable adhesive can be used for this purpose provided that it is compatible with the outermost layers and substrate layers, is permanent, cures as a thin film, and can withstand temperatures up at least about to 150° Fahrenheit. An exemplary adhesive that can be used for this purpose is a room-temperature curing, flexible epoxy. The sensor substrate layers 206 and 214 can be formed of a suitable material, such as polyester or some other materials having similar physical qualities.

An important aspect of the outermost layers 204 and 216 is that their material properties can greatly reduce the shear stresses that the sensory insole may experience at the interface between the conventional insole 104 and the outermost layer 204. Shear stresses introduced between the conventional insole 104 and the outermost layer can adversely impact the performance of the sensor by causing falsely high force measurement readings. Accordingly, use of UMMWPE or a material having similar properties (i.e., low coefficient of friction, self-lubrication, strength and durability) can improve the accuracy of the force measurement obtained by the sensor array.

The exact thickness and type of material chosen for the outermost layers 204, 216 is advantageously selected to limit or allow flexing in accordance with a particular application. A further design consideration with respect to the thickness of these layers involves force distribution among the various sensor cells comprising the array. By carefully selecting the thickness of the outermost layers 204, 216 a designer can facilitate a more consistent distribution of the loading forces to the sensor cells disposed across the surface of the of the sensory array while reducing the effect of point loading. A further purpose of the outermost layers 204, 216 is to effectively increase the cross sectional moment of inertia of the assembly. This is purposefully done in order to minimize sharp bending of the sensory insole for a given force and maximize the radius of any bending. It has been determined that sharp bending can have the adverse effect of altering the output of the sensor. Accordingly, the thickness and material of the outermost layers must be chosen carefully. A suitable thickness of each of the outermost layers 204 and 216 would be in the range from 0.005 inches to 0.060 inches. The exact thickness selected for a particular application will depend on the type of footwear.

Adjacent to each of the sensor substrate layers 206, 214 are top and bottom electrically conductive layers 207, 213. The electrically conductive layers are formed of a metal foil (e.g. copper foil) or from a conductive ink. The top and bottom electrically conductive layers 207, 213 respectively form a plurality of conductive traces which form electrical connections with a plurality of sensor cells 108 as hereinafter described. The electrically conductive layers 207, 213 are electrically isolated from each other by internal electrically insulating adhesive 10 and/or insulating layers 208, 212. Any suitable adhesive can be used for this purpose provided that it demonstrates sufficient adhesion to the adjacent layers, has good durability and has adequate flexibility for a particular insole sensing application. The insulating layers can similarly be formed of any suitable insulating material provided that the material has sufficient durability and flexibility to meet the mechanical requirements of the design. According to one aspect, the top and bottom insulating layers 208, 212 can be formed of a polyester or polyimide film, such as Mylar. The electrically conductive layers can extend substantially continuously across the entire area of the sensory insole, except where perforations 222, 224 are provided (to accommodate the flexing of each cell as hereinafter described). Consequently, each of the individual sensor cells 108 can be advantageously connected in parallel with all other sensor cells between the top and bottom conductive layers 207, 213.

For each sensor cell 108, a plurality of individual pressure sensitive pads are formed of one or more layers of a pressure sensitive ink, 209, 211. For example, two layers of pressure sensitive ink can be used as shown in FIG. 2. The layers of pressure sensitive ink 209, 211 is/are applied in such a manner so that overall thickness variation is kept to a minimum, as such variations can have a direct effect on sensor precision throughout the sensing area. Ideally, the thickness variation of the pressure sensitive ink forming each pressure sensitive pad should be sufficiently controlled so that a resistance value of the pad does not vary by more than about ten percent for a given fixed load applied to each cell. According to one aspect, the pressure sensitive ink can be comprised of a piezoelectric material that produces a resistance value which varies in accordance with an applied pressure. Such piezoelectric type pressure sensitive inks as described herein are well known in the art and therefore will not be described here in detail. Any suitable pressure sensitive ink can be used for this purpose provided that it is sufficiently reactive to changes in pressure and has sufficient durability.

From the foregoing it will be understood that the arrangement of the pressure sensitive pads, electrically conductive layers, insulating adhesives 210 and/or insulating layers 208, 212 are arranged such that a plurality of individual sensor cells are formed in a particular repetitive pattern to define an array. In the embodiment shown, each pad is rectangular or square, but it should be appreciated that the invention is not limited in this regard. Accordingly, each pressure sensitive pad can have a particular geometric shape such as squares, circles, spirals, or any other desired shape/s disposed on the substrate. Each such sensor cells will be separated by a gap from adjacent cells such that the assembled sensor includes interstitial areas 218, 220 which will not register any force.

Figure 3:
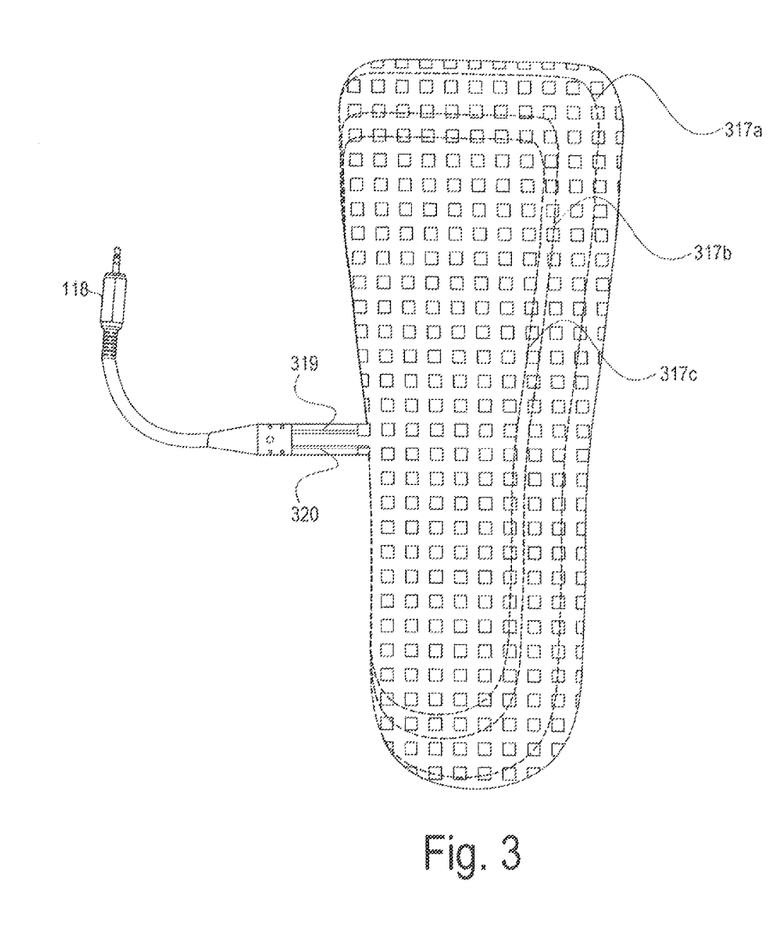
FIG. 3 is a top view of the sensory insole in FIG. 1 that is useful for understanding how the sensor can be trimmed to any shape without damaging the sensor.

The particular repetitive pattern that is used for the arrangement of the sensor cells can be a linear grid pattern in which sensor cells 108 are arranged in linear rows and columns as shown in FIG. 3. However, the invention is not limited in this respect and other repetitive patterns are also possible without limitation. For example, in some embodiments, the sensor cells in each adjacent row or column can be slightly offset in position from a preceding row. Likewise, rows and columns of sensor cells can be aligned along a diagonal line rather than orthogonally as shown in FIG. 3. Although the particular repetitive pattern selected is not critical, the size of each cell and the pattern should be chosen so that the individual sensor cells 108 are densely packed and much smaller in area as compared to the area of the sensory insole as a whole. For example, the density of sensor cells to overall area of the sensory insole should be in the range of 10%-40% depending on application The repetitive pattern and arrangement of each of the layers comprising the sensory insole allows it to be cut and trimmed to any size or shape to fit the insole areas of multiple footwear types (such as a sneaker, cast or cam walker) and still properly function as a sensory insole capable of measuring force exerted by a user through a limb. This concept is illustrated in FIG. 3, which shows various trim lines 317a, 317b, 317c which can be used when trimming a sensory insole 102, without negative effect upon its sensing function.

The repetitive pattern of the sensor cells and the above-described manner in which they are electrically connected, allows for the possibility of perforation and or removal of various peripheral areas of the sensor array without damaging its force sensing capability. The arrangement of the conductive traces is such that the trimming or removal of certain sensor cells by cutting away peripheral portions of the sensory insole (or by perforation of interior areas the sensory insole) does not disrupt the electrical connections to the remaining sensor cells. Accordingly, the remaining sensor cells and the sensory insole as a whole remains fully functional when portions of the insole are perforated or peripheral areas are trimmed. This feature is advantageous in the context of an insole because different shoe sized for different persons can require insoles of different size.

The sensory insole 102 can be trimmed down (i.e. portions cut-away around an outer perimeter) to eliminate as many sensor cells 108 as needed to fit a particular footwear application, provided that the connections provided by conductors 319, 320 from the upper and lower conductive layers 207, 213 to jack 118 are not cut. Likewise, interior areas of the sensory insole, within the outer perimeter, can be removed to accommodate a particular use application. Such cutting of perimeter or interior areas of the sensory array will not adversely affect the performance of the sensory insole. As illustrated in FIG. 2 conductive layers 207, 213 comprise conductive flat wire traces extending substantially over the entire surface area of the sensory insole. When pressure is applied to pressure sensitive ink layers 209 and 211 it causes a reduction in resistance as measured between the conductive layers. As may be understood from FIG. 2 one can cut any shape to fit an insole because the conductive layers 207 and 213 extend in a substantially continuous way throughout the entire area of the sensory insole 102.

When low pressure is applied to layers 209 and 211 a relatively high resistance is obtained. As more pressure is applied to layers 209 and 211 resistance between the two layers is reduced. This variable resistance property can be used to vary a voltage drop across the conductive layers 207, 213 and this variation can be measured or determined at a control unit as hereinafter described to determine an amount of force being applied to the sensory insole 102.

Figure 4:
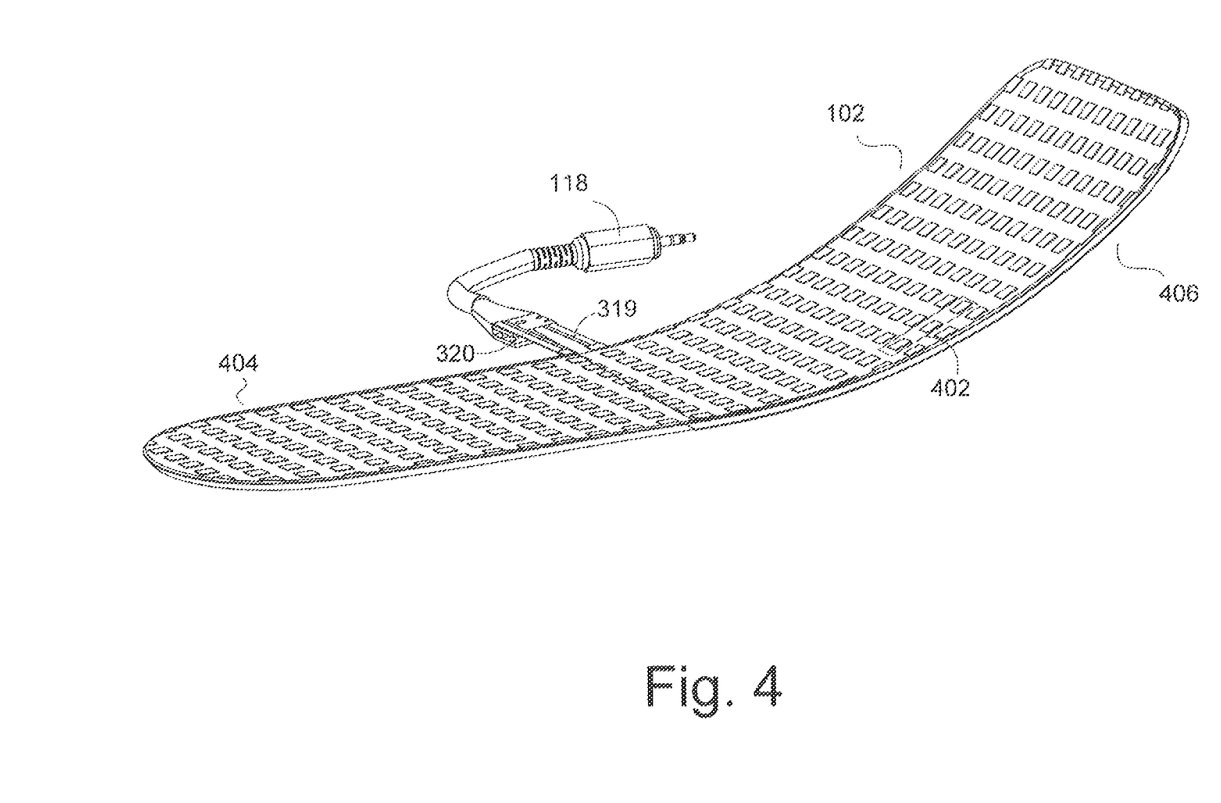
FIG. 4 is a drawing that is useful for understanding the manner in which the construction of the sensory insole in FIG. 1 can facilitate flexing.

Referring once again to FIG. 2, it can be observed that each layer comprising the sensory insole 102 includes a repetitive pattern of perforations 222, 224, 226, 228, 230, 234, 236, 238, 240, 242. It may be observed that the perforations are present in all layers except for 209, 210 and 211 of FIG. 2. The "perforations" are the cut away areas in each layer. The perforations function to allow additional degrees of freedom within the perimeter of the sensory insole, thereby allowing it to flex more freely as shown in FIG. 4, without creasing. This improved ability to flex allows the sensory insole 102 to better conform to irregular surfaces, thereby increasing pressure measurement accuracy. This concept is best understood with reference to FIGS. 5 and 6 which show the manner in which the perforations allow portions of individual sensor cells 108 to move or pivot independently from other portions of the substrate.

Figure 5:
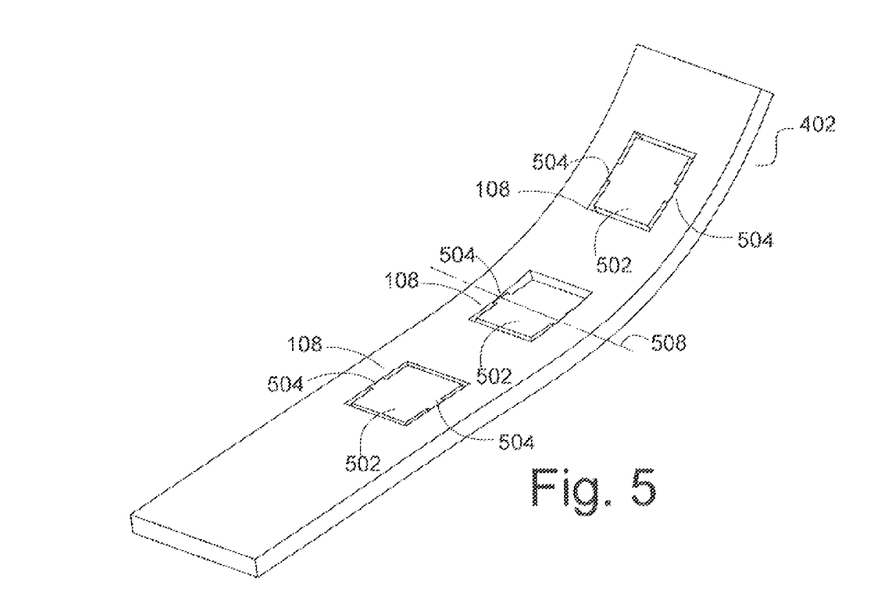
FIG. 5 is an enlarged view of a portion of the sensory insole, illustrating the functions of the perforations in the sensing area while under flex.
Figure 6:
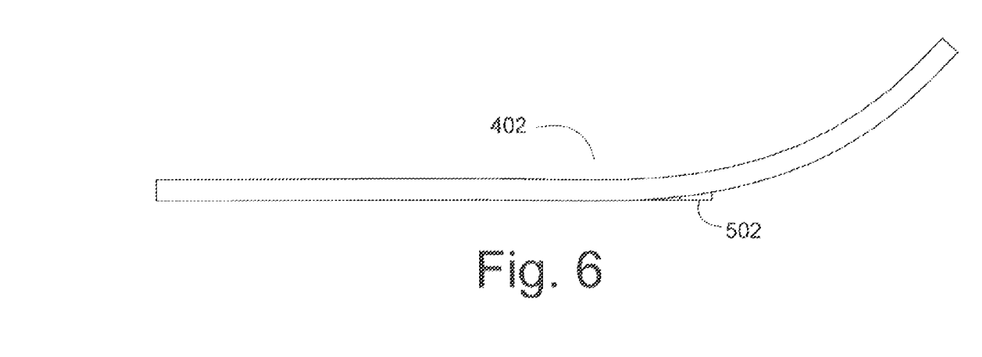
FIG. 6 is a side view of the portion of the sensor insole layer in FIG. 5.

FIGS. 5 and 6 show an enlarged area 402 of the sensory insole 102, with all layers assembled, and including three of the sensor cells 108. It can be observed in FIGS. 5 and 6 that the perforations define individually cut polygons 502 within which each sensor cell 108 is disposed. In the exemplary embodiment shown, the cut polygons are square or rectangular, but the invention is not limited in this regard. The perforations can optionally define instead circles or other polygon shapes. The cut polygons defined by the perforations in the insole facilitate an added degree of movement of a portion of the insole. More particularly, the perforations form opposing hinge members 504 on opposing sides of the cut polygon that define an axis of rotation 508 about which each cut polygon can rotate. The cut polygon 502 associated with each sensor cell 108 allows the cell to move relative to the remainder of the substrate defining the sensory insole 102. The arrangement advantageously inhibits bending of the ink pads 208, 211 which comprise the actual sensing areas associated with each sensor cell 108.

It can be observed in FIGS. 5 and 6 that the perforations are arranged to physically release each sensor cell 108 from the larger sensory insole. The hinge members 504 support and maintain the position of each sensor cell 108 within the sensor array, but have the added benefit of allowing the portions of each sensor cell to pivot independently from the larger substrate to which they are attached. The hinge members also facilitate transmission of electrical current to and from each sensor 108 through the conductive layers 207, 213. The hinge members allow each sensor cell to rotate about the sensor axis 508 without distorting the sensing layers. The result is that physical distortion of each sensor cell can be minimized during conditions of sensory insole flexing, and measurement accuracy is improved. The pivot axis of each sensory cell can be advantageously chosen so that it is aligned in a way that minimizes sensor cell flexing. For example, the pivot axis can be selected to be transverse to an elongated length of the insole since insole flexing usually occurs from front to back of an insole and a pivot axis aligned transverse to this direction will help minimize physical distortion of each cell.

According to one aspect of the invention, the pivot axis of all sensor cells can be aligned. However, the invention is not limited in this regard and in some scenarios it may be advantageous to vary the alignment of the pivot axis in accordance with different areas of the insole that are known to flex in different ways. Accordingly, sensor cells in a first section of the insole may all have their pivot axis aligned in a first direction whereas sensor cells in a second section (different from the first section) may have their pivot axis aligned in a second direction which is different from the first direction. For example, sensor cells in heel area 404 of the insole can have a pivot axis aligned in the first direction and sensor cells in a ball area 406 can have sensor cells with a pivot axis aligned in the second direction.

As shown in FIGS. 3 and 4, a sensory insole 102 as described herein can require only two electrical conductors 319, 320 for purposes of communicating force sensing information to a control unit as hereinafter described. A first one of the electrical conductors 319 can be connected to the top conductive layer 207 and a second one of the electrical connections 320 can be connected to a bottom conductive layer 213. According to one aspect of the inventive arrangements, the individual sensor cells 108 are connected in parallel between the top and bottom conductive layers 207, 213. A terminating jack 118 can be used to couple the electrical conductors to a control unit. By requiring only two conductors for a sensory insole comprised of a multitude of sensor cells 108, it is possible to facilitate a less intrusive interface between the sensory insole and a control unit as hereinafter described. Such a less intrusive interface can be advantageous for improving comfort of a user.

According to a further aspect, a sensory insole control unit provides a regulated voltage output to the sensory insole. The regulated voltage output provided by the sensory insole control unit is applied to the sensory insole via electrical conductor 319, 320. For example, conductor 319 can be electrically connected to the top electrically conductive layer 207 and conductor 320 can be electrically connected to the bottom electrically conductive layer 213. Accordingly, the regulated voltage from the control unit is applied across the network of sensor cells, which are electrically connected in parallel. The control unit directly or indirectly detects changes in resistance associated with the network of sensor cells by detecting variations in current or variations in the voltage drop which occurs across the network. The control unit can use this raw voltage or current data to estimate a total applied force applied to the sensor. For example, the measured data can be used in conjunction with a look-up table stored in memory that equates various measured values with predetermined levels of applied force.

Figure 7:
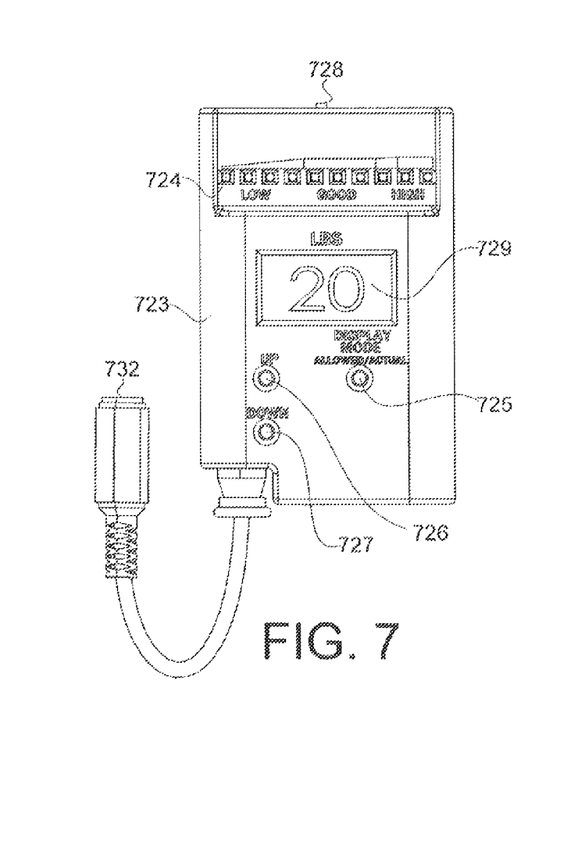
FIG. 7 is a front view of a control module which can be used with the sensor in FIG. 1.
Figure 8:
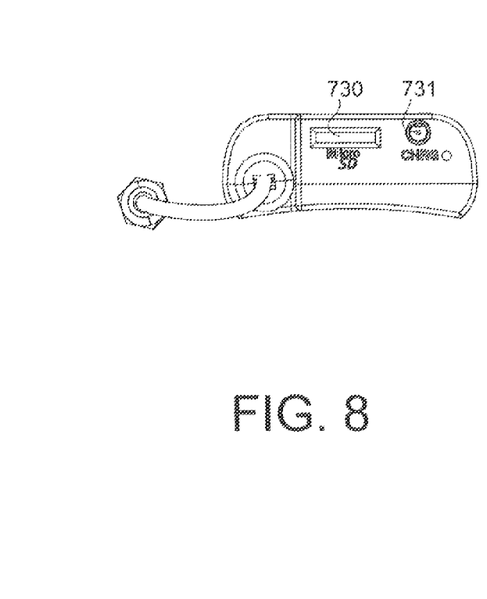
FIG. 8 is a bottom view of the control module of FIG. 7.
Figure 9:
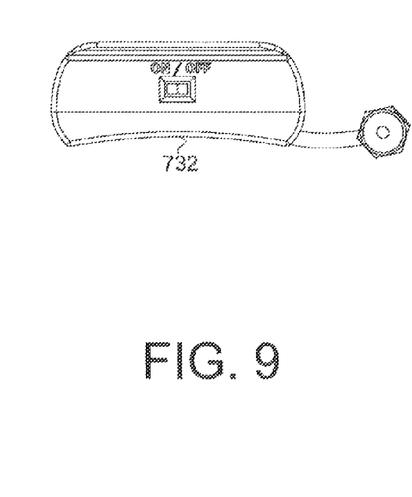
FIG. 9 is a top view of the control module of FIG. 7.
Figure 10A:
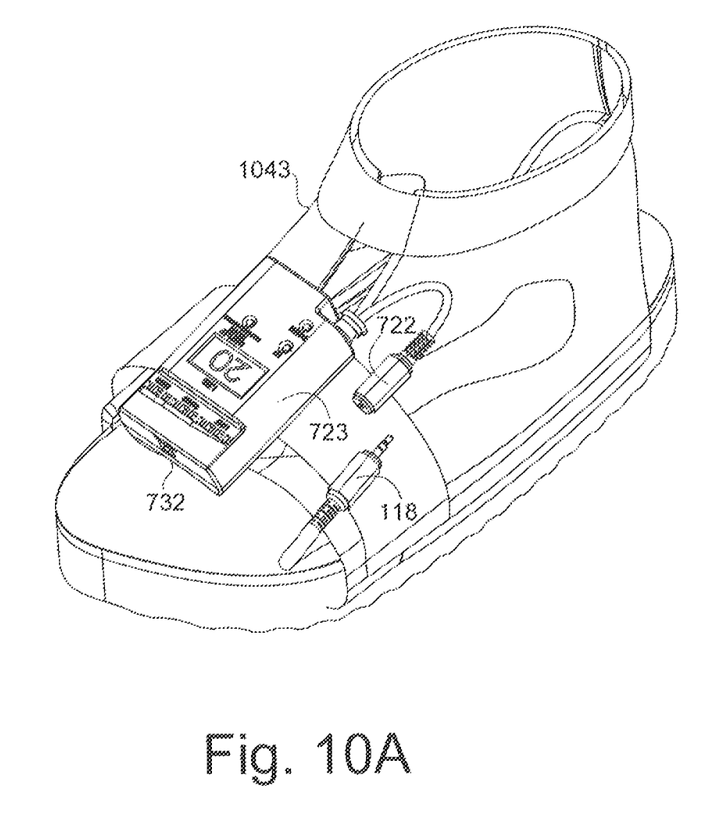
FIGS. 10A-10C are a set of drawings that are useful for showing the various ways that the control module of FIG. 7 could be mounted on various footwear types, remote from the sensory insole.
Figure 10B:
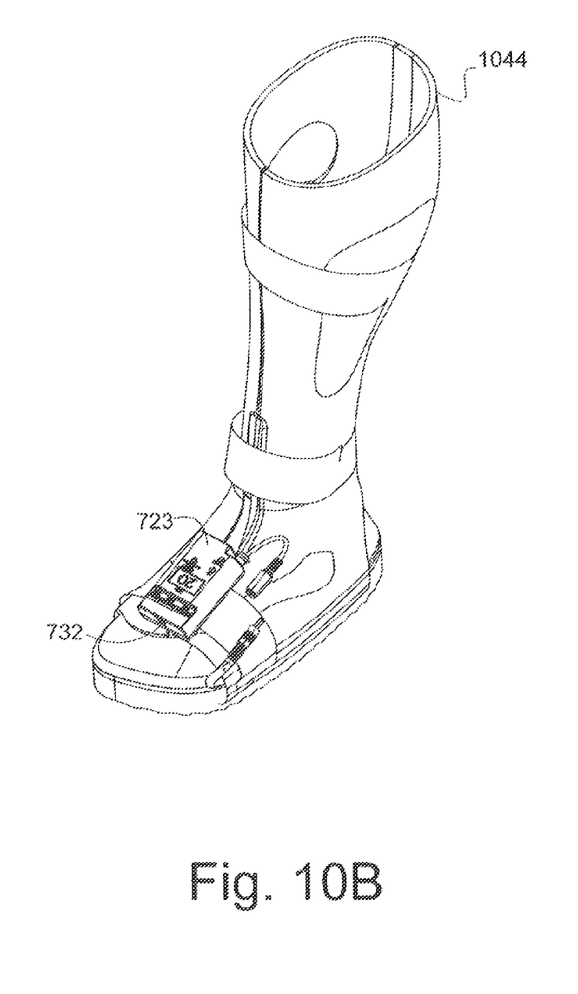
Figure 10C:
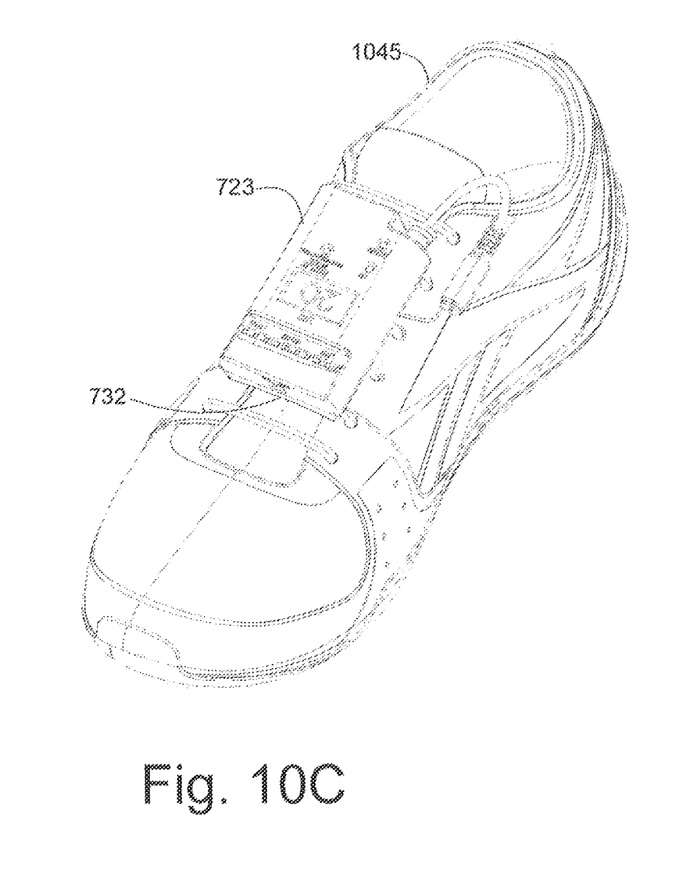

An exemplary control unit 723 is shown in FIGS. 7-9. The control unit 723 is an assembly containing necessary electrical components to perform the functions and operations described herein. As such, the control unit 723 can include a mating plug 722 for receiving therein the terminating jack 118. The mating plug can be located on or may be connected to the control unit as shown. The mating plug and terminating jack facilitate forming an electrical connection with the network of sensor cells 108 comprising the sensory insole 102. This connection arrangement allows the sensory insole 102 to be selectively removably connected or disconnected to the control unit 723 by a user. The housing of the control unit 723 advantageously has an ergonomic shape to allow for multiple mounting schemes. For example, the housing can include a concave face 732 which facilitates mounting of the control unit in various usage scenarios. As shown in FIGS. 10A, 10B and 10C, the concave face 732 can facilitate a snug engagement of the control unit 723 on a cast walker 1043, a cam walker 1044, a sneaker 1045, or other types of footwear. The snug fit in each scenario is due in part to the curved form of the concave face 732, which generally matches a curved mounting surface associated with each type footwear, while minimizing any intrusion to the patient. In each scenario, the control unit is fastened to the top of the footwear via hook and loop fabric fasteners or by other suitable means. The control unit is also electrically connected as described herein to the sensory insole 102 which is placed inside the footwear.

One or more tactile buttons and/or switches 725, 726, 727, 728 can be provided on one or more faces of the control unit 723. These tactile devices can be used for selecting or changing various settings on the control unit. For example, they may be operated by a user to input desired force set points (e.g. for maximum allowable force), selection of various modes the device can operate in, recalibration, and for activation/deactivation of certain features/sensory notifications. An alphanumeric display 729 provides a means to verify or convey to the user what information is being inputted.

Figure 11:
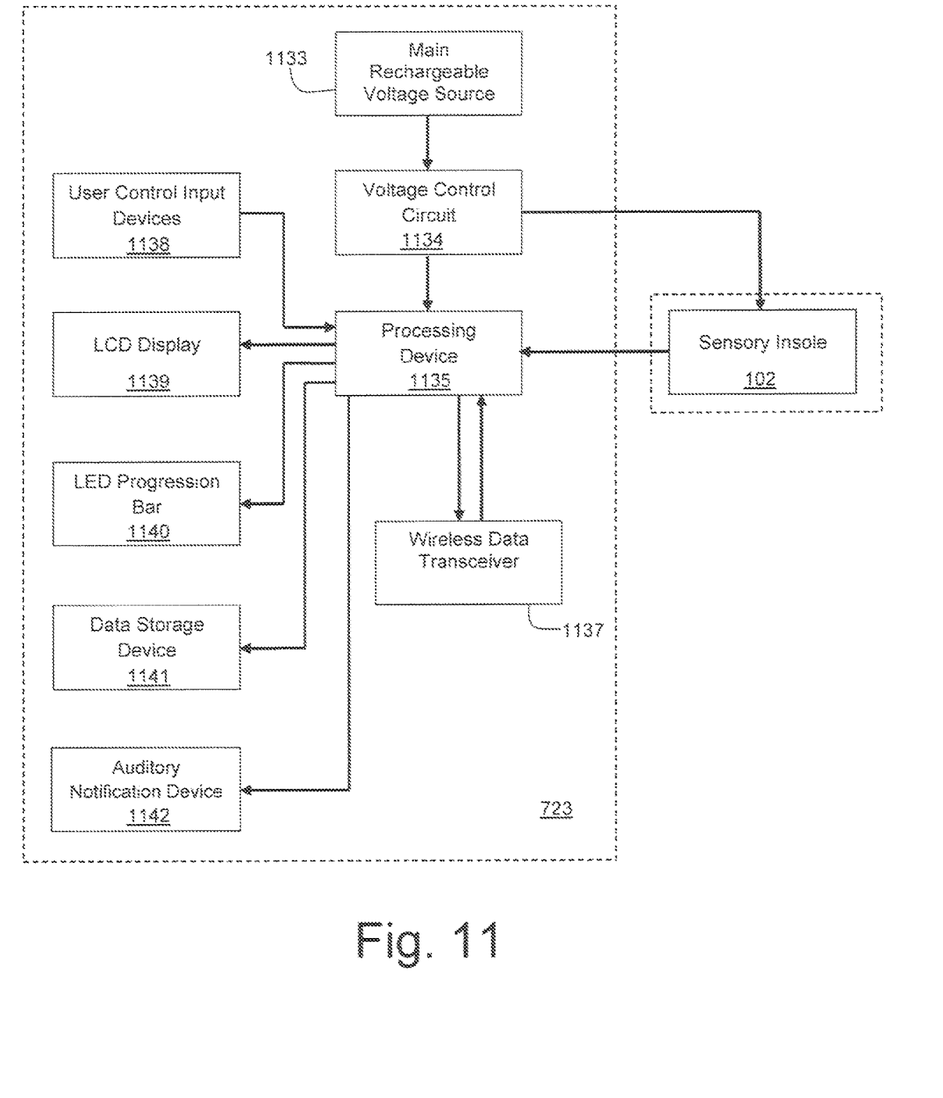
FIG. 11 is a simplified block diagram that is useful for understanding the operation of the control unit.

A block diagram provided in FIG. 11 is useful for understanding an exemplary arrangement of the control system 723 and the sensory insole 102. As illustrated therein, the control unit includes a power source 1133, processing device 1135, a voltage control circuit 1134, and user control input devices 1138. Also provided in or on the control unit are integral visual and/or audio notification devices. For example, the control unit can include one or more of an alphanumeric display (e.g. a liquid crystal type alphanumeric display) 1139, an LED progression bar 1140, and an auditory notification device 1142. The control unit also includes a data storage device 1141 and a wireless transceiver 1137. Each of the functional blocks comprising the control unit is discussed in more detail below.

The processing device 1135 can be any suitable data processing device that is capable of receiving analog voltage outputs derived from the sensory insole, and processing such voltage outputs so as to thereafter selectively perform the various operations described herein. Accordingly, the processing device 1135 can be a microcontroller, a Field Programmable Gate Array (FPGA), a central processing unit (CPU) or any other suitable processing device. The voltage control circuit 1134 is designed to facilitate the application of a predetermined regulated voltage to the sensor assembly 1136. For measurement purposes, it will be appreciated that a precisely regulated voltage applied to the sensor assembly is advantageous because it facilitates greater measurement accuracy.

Figure 12:
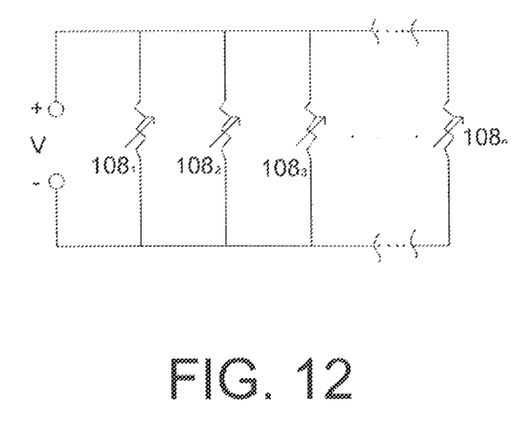
FIG. 12 is a circuit diagram that is useful for understanding the electrical connections among a plurality of sensor cells comprising the sensory insole.

Referring now to FIG. 12, there is illustrated a network 1200 of sensor cells $108_1$, $108_2$, $108_3$, ... $108_n$ connected in parallel as described herein. Each sensor cell has a resistance which is varies in a predetermined manner based on the amount of pressure exerted upon it. The resistance of the network will therefore vary in a predetermined way based on the pressure applied to individual sensor cells. The control unit applies a voltage V to the network 1200 across the plurality of sensor cells as shown for purposes of determining these variations in resistance. In this regard it may be appreciated that the control unit relies upon variations in resistance of a network of sensor cells 108 to estimate a force applied to the sensory insole 102. The control unit determines the resistance based on either a voltage drop across the network or based on variations in current flow through the network. Unanticipated variations in the voltage V applied to the network can produce erroneous resistance measurements. Consequently, the voltage applied to the network of sensor cells is advantageously regulated with a high degree of precision.

The progression bar 1140 can be comprised of an array of light emitting diodes (LEDs) 724 arranged in a linear fashion as shown in FIG. 7. The processing device can be arranged to cause the LEDs in the light bar array to progressively illuminate in real time based on the percentage of a predetermined or preset force that is measured by the sensory insole. This progression bar is advantageous in allowing the patient to more accurately achieve their desired force per step. By clearly visualizing the "approach" to the desired force range, patient accuracy and precision in achieving their desired force per step is greatly improved. These LED's also serve to notify the user if the applied force is greater than the desired force. In some embodiments, the progression bar can be complimented by an auditory signal generated by auditory notification device 1142 when a predetermined level of force has been achieved or exceeded. The audio notification device 1142 can be any suitable device capable of generating an audio tone when activated. The audio notification device can optionally be disabled by the processing device 1135 if such a preference is specified by the user.

The data storage device 1141 can be any suitable device for storing force measurement data extracted by the processing unit 1135 from outputs of the sensory assembly 1136. For example, the data storage device can be an electronic memory storage system comprised of random access memory (RAM) circuits. According to one aspect, the data storage device can be comprised of a removable memory card 730 to facilitate remote analysis of the recorded data on a separate computing system. The data processing unit 1135 can be programmed to periodically cause force measurement data to be stored in the data storage device. According to another aspect, the data processing unit 1135 can be programmed to store information corresponding to forces measured with each step a patient takes. In response to a user command, the microcontroller can facilitate a wireless downloading of such data to a connected computer system for later analysis. For example, such data can be transferred to a connected computer system using the wireless data transceiver 1137.

The wireless transceiver 1137 can be any suitable device capable of communicating data to a connected computer system, such as a smart phone. The wireless transceiver can advantageously also receive data and configuration settings from the connected computer system for simplifying operation of the control system 723. For example, a user might use a connected computer system to specify for the control system certain alarm set points (such as maximum permitted force levels), times when data is to be recorded, amounts of data to be recorded, frequency of data recordation, alarm configurations (audio notification on/off) and so on. These settings can be communicated to the control system using the wireless transceiver 1137. A wireless transceiver 1137 as described herein can use any suitable communication protocol for communicating data over an air interface. For example, the wireless transceiver can implement a Bluetooth wireless technology standard for exchanging data over short distances.

Those skilled in the art will appreciate that the system architecture illustrated in FIG. 11 is one possible example of a control unit that can be used with the present invention. However, the invention is not limited in this regard and any other suitable control unit architecture can also be used without limitation. Dedicated hardware implementations including, but not limited to, application-specific integrated circuits, programmable logic arrays, and other hardware devices can likewise be constructed to implement the methods described herein. Applications that can include the apparatus and systems of various embodiments broadly include a variety of electronic and computer systems. Some embodiments may implement functions in two or more specific interconnected hardware modules or devices with related control and data signals communicated between and through the modules, or as portions of an application-specific integrated circuit. Thus, the exemplary system is applicable to software, firmware, and hardware implementations.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Thus, the breadth and scope of the present invention should not be limited by any of the above described embodiments. Rather, the scope of the invention should be defined in accordance with the following claims and their equivalents.

We claim:

1. A lower limb force sensing system, comprising:
a sensory insole formed of a plurality of thin film material layers arranged in a stack to form a plurality of sensor cells arranged in a pattern to define a sensor array, each of said sensor cells comprised of a pressure sensitive pad disposed between opposing top and bottom electrically conductive layers;
a plurality of perforations defined in the thin film material layers which extend substantially around a perimeter of each sensor cell to substantially separate each sensor cell from a remainder of the thin film material layers forming the sensory insole, the plurality of perforations defining for each sensor cell at least one hinge member which extends from each sensor cell to an interstitial portion of the thin film layers extending between adjacent ones of the sensor cells;
wherein said at least one hinge member comprises electrical connections respectively between portions of the top and bottom electrically conductive layers disposed in said interstitial portion of the thin film layers and the top and bottom electrically conductive layers disposed within the perimeter of each sensor cell, and said at least one hinge member defines an axis of rotation about which the sensor cell can pivot independently relative to adjacent interstitial portions of the thin film material layers.

2. The lower limb force sensing system according to claim 1, wherein the pressure sensitive pad is comprised of a piezoresistive material.

3. The lower limb force sensing system according to claim 1, wherein the plurality of thin film material layers are further comprised of top and bottom outermost layers formed of a low-coefficient of friction material.

4. The lower limb force sensing system according to claim 3, wherein at least one of the top and bottom outermost layers are formed of ultra-high-molecular-weight polyethylene (UHMWPE).

5. The lower limb force sensing system according to claim 1, wherein the top and bottom electrically conductive layers extend coextensive with said sensor array to provide continuity to the electrical connections of each of said sensor cells.

6. The lower limb force sensing system according to claim 5, wherein the plurality of sensor cells are connected in parallel between the top and bottom electrically conductive layers.

7. The lower limb force sensing system according to claim 6, wherein the top and bottom electrically conductive layers maintain continuity with said electrical connections of all the sensor cells on a remaining portion of the sensory insole when unwanted portions of the material layers of the sensory insole have been cut away from the remaining portion.

8. The lower limb force sensing system according to claim 6, further comprising a control unit remote from the sensory insole which detects electrical changes occurring within the plurality of sensor cells based on a changes in at least one electrical characteristic of the plurality of sensor cells responsive to changes in force applied to the sensory insole.

9. The lower limb force sensing system according to claim 8, wherein the control unit is electrically connected to the sensory insole with only two electrical conductors, including a first electrical conductor connected to the top electrically conductive layer and a second electrical conductor connected to the bottom electrically conductive layer.

10. The lower limb force sensing system according to claim 9, wherein said remote control system is removably electrically connected to the two conductors using a jack and plug arrangement.

11. The lower limb force sensing system according to claim 8, wherein the electrical characteristic which is changed responsive to changes in force is a resistance between the top and bottom electrically conductive layers.

12. The lower limb force sensing system according to claim 8, wherein the control unit comprises a regulated voltage source which is connected to two electrical conductors and a processing device which determines a force exerted on the sensory insole responsive to variations in voltage drop occurring across the two electrical conductors.

13. The lower limb force sensing system according to claim 12, wherein said control unit further comprises a data storage device and at least one wireless transceiver for communicating pressure data stored in the data storage device by the processing device to a remote computing device.

14. The lower limb force sensing system according to claim 8, wherein the control unit includes at least one progression bar comprised of a plurality of illuminable elements which progressively illuminate in response to increases in force applied to the sensory insole.

15. The lower limb force sensing system according to claim 14, wherein the control unit includes an auditory device which is responsive to the processing device to produce an auditory signal when a predetermined force applied to the sensory insole has been met or exceeded.

16. A method for improving a measurement accuracy when using a sensory insole, comprising:
providing a sensory insole formed of a plurality of thin film material layers arranged in a stack to form a plurality of sensor cells arranged in a pattern to define a sensor array, where each of said sensor cells comprised of a pressure sensitive pad disposed between opposing top and bottom electrically conductive layers;
forming a plurality of perforations defined in the thin film material layers which extend substantially around a perimeter of each sensor cell to substantially separate each sensor cell from a remainder of the thin film material layers forming the sensory insole;
forming with the plurality of perforations at least one hinge member for each sensory cell which extends from each sensor cell to an interstitial portion of the thin film layers extending between adjacent ones of the sensor cells;
pivoting one or more of said plurality of sensor cells independently relative to adjacent interstitial portions of the thin film material layers when said sensory insole is placed in footwear, said pivoting occurs about an axis of rotation about defined by the at least one hinge member.

17. The method according to claim 16, further comprising reducing a measurement error associated with the sensory insole by including in the plurality of thin film material layers top and bottom outermost layers formed of a low-coefficient of friction material.

18. The method according to claim 17, further comprising selecting the low-coefficient of friction material to be an ultra-high-molecular-weight polyethylene (UHMWPE).

19. The method according to claim 16, further comprising electrically connecting the plurality of sensor cells in parallel between the top and bottom electrically conductive layers.

20. The method according to claim 19, further comprising determining a force applied to the sensory insole using a remotely situated control unit, that is electrically connected to the top and bottom electrically conductive layers, by detecting a variation in electrical resistance as between the top and bottom electrically conductive layers.

21. The method according to claim 20, further comprising guiding a user to a predetermined force exerted on the sensory insole by progressively illuminating a plurality of illuminable elements comprising a progression bar in response to increases in force applied to the sensory insole.

* * * * *